(12) United States Patent
Sun et al.

(10) Patent No.: US 11,944,603 B2
(45) Date of Patent: Apr. 2, 2024

(54) USE OF COMPOUND OR MEDICINAL DERIVATIVE THEREOF IN INHIBITING AIM2 PROTEIN ACTIVITY

(71) Applicant: Liangdan Sun, Hefei (CN)

(72) Inventors: Liangdan Sun, Hefei (CN); Qi Zhen, Hefei (CN); Bao Li, Hefei (CN)

(73) Assignee: Liangdan Sun, Hefei (CN)

( * ) Notice: Subject to any disclaimer, the term of this patent is extended or adjusted under 35 U.S.C. 154(b) by 0 days.

(21) Appl. No.: 17/837,344

(22) Filed: Jun. 10, 2022

(65) Prior Publication Data
US 2023/0321047 A1    Oct. 12, 2023

(30) Foreign Application Priority Data

Apr. 6, 2022    (CN) .......................... 202210355367.X

(51) Int. Cl.
*A61K 31/4184*    (2006.01)
*A61P 17/06*    (2006.01)

(52) U.S. Cl.
CPC .......... *A61K 31/4184* (2013.01); *A61P 17/06* (2018.01)

(58) Field of Classification Search
CPC ........................... A61K 31/4184; A61P 17/06
See application file for complete search history.

(56) References Cited

PUBLICATIONS

Registry-Results, 2023.*

* cited by examiner

*Primary Examiner* — Shobha Kantamneni
(74) *Attorney, Agent, or Firm* — WPAT, P.C.

(57) ABSTRACT

A use of a compound or a medicinal derivative thereof in inhibiting absent in melanoma 2 (AIM2) protein activity is provided, and belongs to the field of protein inhibitory medicine technology. Compared with traditional broad-spectrum immunomodulators, the compound has a strong targeting effect, and is more accurate, rapid, effective, safe and stable. Moreover, the compound has a strong binding force with human AIM2 protein and mouse AIM2 protein, and binding constants are as high as 1.029E-5M and 1.033E-5M respectively. Compared with traditional biological inhibitors, the compound has advantages of easy storage, stable activity, small molecular weight, lower production cost and easy absorption.

15 Claims, 13 Drawing Sheets

Specification includes a Sequence Listing.

SEQUENCE LISTING

```
<160> NUMBER OF SEQ ID NOS: 1

<210> SEQ ID NO 1
<211> LENGTH: 343
<212> TYPE: PRT
<213> ORGANISM: Artificial Sequence
<220> FEATURE:
<223> OTHER INFORMATION: AIM2

<400> SEQUENCE: 1

Met Glu Ser Lys Tyr Lys Glu Ile Leu Leu Leu Thr Gly Leu Asp Asn
1               5                   10                  15

Ile Thr Asp Glu Glu Leu Asp Arg Phe Lys Phe Phe Leu Ser Asp Glu
            20                  25                  30

Phe Asn Ile Ala Thr Gly Lys Leu His Thr Ala Asn Arg Ile Gln Val
        35                  40                  45

Ala Thr Leu Met Ile Gln Asn Ala Gly Ala Val Ser Ala Val Met Lys
    50                  55                  60

Thr Ile Arg Ile Phe Gln Lys Leu Asn Tyr Met Leu Leu Ala Lys Arg
65                  70                  75                  80

Leu Gln Glu Glu Lys Glu Lys Val Asp Lys Gln Tyr Lys Ser Val Thr
                85                  90                  95

Lys Pro Lys Pro Leu Ser Gln Ala Glu Met Ser Pro Ala Ala Ser Ala
```

```
              100                 105                 110
Ala Ile Arg Asn Asp Val Ala Lys Gln Arg Ala Ala Pro Lys Val Ser
            115                 120                 125
Pro His Val Lys Pro Glu Gln Lys Gln Met Val Ala Gln Gln Glu Ser
            130                 135                 140
Ile Arg Glu Gly Phe Gln Lys Arg Cys Leu Pro Val Met Val Leu Lys
145                 150                 155                 160
Ala Lys Lys Pro Phe Thr Phe Glu Thr Gln Glu Gly Lys Gln Glu Met
                165                 170                 175
Phe His Ala Thr Val Ala Thr Glu Lys Glu Phe Phe Phe Val Lys Val
            180                 185                 190
Phe Asn Thr Leu Leu Lys Asp Lys Phe Ile Pro Lys Arg Ile Ile Ile
            195                 200                 205
Ile Ala Arg Tyr Tyr Arg His Ser Gly Phe Leu Glu Val Asn Ser Ala
            210                 215                 220
Ser Arg Val Leu Asp Ala Glu Ser Asp Gln Lys Val Asn Val Pro Leu
225                 230                 235                 240
Asn Ile Ile Arg Lys Ala Gly Glu Thr Pro Lys Ile Asn Thr Leu Gln
                245                 250                 255
Thr Gln Pro Leu Gly Thr Ile Val Asn Gly Leu Phe Val Val Gln Lys
                260                 265                 270
Val Thr Glu Lys Lys Lys Asn Ile Leu Phe Asp Leu Ser Asp Asn Thr
            275                 280                 285
Gly Lys Met Glu Val Leu Gly Val Arg Asn Glu Asp Thr Met Lys Cys
        290                 295                 300
Lys Glu Gly Asp Lys Val Arg Leu Thr Phe Phe Thr Leu Ser Lys Asn
305                 310                 315                 320
Gly Glu Lys Leu Gln Leu Thr Ser Gly Val His Ser Thr Ile Lys Val
                325                 330                 335
Ile Lys Ala Lys Lys Lys Thr
                340
```

USE OF COMPOUND OR MEDICINAL DERIVATIVE THEREOF IN INHIBITING AIM2 PROTEIN ACTIVITY

TECHNICAL FIELD

The disclosure relates to the field of protein inhibitory medicine technologies, and more particularly to a use/application of a compound or a medicinal derivative thereof in inhibiting absent in melanoma 2 (AIM2) protein activity.

BACKGROUND

Psoriasis is a global, refractory, high incidence rate inflammatory-immune disease, which cannot be completely cured under a current medical level. There are many clinical treatments for psoriasis, most of which attempt to alleviate symptoms through extensive inhibition of an immune system, such as uses of hormones and immunosuppressants, and uses of some physical therapy and traditional Chinese medicine. However, broad-spectrum symptomatic treatment is often ineffective, which is very easy to cause repeated illness or other system damage. In recent years, the development of precision medicine for psoriasis has made up for shortcomings of traditional treatment regimens to a certain extent, and many biological agents have been developed to target effector molecules downstream of an inflammatory pathway of psoriasis, such as interleukin 17 (IL-17), tumor necrosis factor alpha (TNF-α), and interleukin 23 (IL-23), in an attempt to eliminate a phenotype of psoriasis.

Compared with the traditional treatment regimens, the biological agents can increase a cure rate of patients with psoriasis to varying degrees over a period of time, with longer dosing interval and greater compliance. However, it has same disadvantages as the traditional treatment regimens. At present, all biological agents for psoriasis on the market are still symptomatic treatments that fundamentally reduce the phenotype by blocking efficacy of downstream effector molecules. If uses of the biological agents are stopped for more than half a year, the risk of psoriasis recurrence will be greatly increased. In addition, the biological agents are expensive, because of the need for long-term maintenance of medication, if the effect is weakened halfway, a variety of biological agents should be used in combination, which brings a greater economic burden to patients.

To sum up, medicines currently used in the treatment of psoriasis can be divided into two main types including broad-spectrum immunomodulatory medicines and targeted medicines. The long-term effect of traditional broad-spectrum immunomodulatory medicines is not ideal. The targeted medicines represented by biological agents make up for lacks of efficacy of traditional medicines to a certain extent, but the biological agents are expensive and have relatively high applicable standards. There are few other types of targeted medicines (natural small molecules or artificial compounds) for psoriasis on the market, and almost all of them target a downstream effector pathway in the pathogenesis of psoriasis, which has a weak impact on a key cytokine IL-17 and its upstream initiation pathway. Compared with the treatment that interferes with factors of an upstream of the inflammatory pathway of psoriasis, the long-term effect of this symptomatic treatment may not be good.

Therefore, it is imperative to develop new medicines that complement advantages of traditional treatment and the biological agents, not only to make up for the shortcomings of the above medicines, but also to take into account the effectiveness, targeting, economy, safety, compliance of medicines.

SUMMARY

A purpose of the disclosure is to provide a use of a compound or a medicinal derivative thereof in inhibiting absent in melanoma 2 (AIM2) protein activity. The compound can be used as a medicine for treating psoriasis, which can significantly inhibit production of interleukin 1 beta (IL-1β), reduce proportions of TCRγ/CD3+RORγt of imiquimod (IMQ) mice, significantly improve an inflammatory phenotype of the IMQ mice.

Specifically, the compound ($C_{28}H35N_3O_3$) is shown in formula I, and the formula I is expressed as follows:

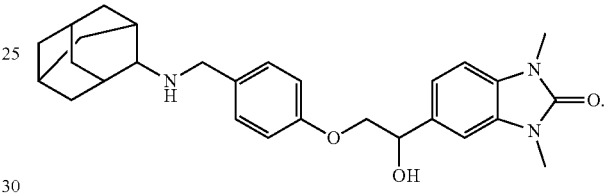

formula I

In an aspect, the disclosure provides a use of the compound or a medicinal derivative thereof in inhibiting AIM2 protein activity.

In an illustrated embodiment of the use of the disclosure, the compound is in the form of a pharmaceutical salt.

In an illustrated embodiment of the use of the disclosure, the compound is in the form of a pharmaceutical acid addition salt.

In another aspect, the disclosure provides an application method of the compound or the medicinal derivative thereof in preparing a medicine for inhibiting AIM2 protein activity.

In an illustrated embodiment of the application method of the disclosure, the medicine for inhibiting the AIM2 protein activity is a medicine of inhibiting the AIM2 protein activity of psoriatic lesion tissue.

In an illustrated embodiment of the application method of the disclosure, the compound is in a form of a pharmaceutical salt.

In an illustrated embodiment of the application method of the disclosure, the compound is in a form of a pharmaceutical acid addition salt.

In an illustrated embodiment of the application method of the disclosure, a dosage form of the medicine inhibiting AIM2 protein activity is at least one selected from a group consisting of a capsule, a tablet, an oral preparation, a microcapsule preparation, an injection, a suppository, a spray, and an ointment.

In still another aspect, the disclosure provides a pharmaceutical composition for treating psoriasis, which including at least a compound as shown in formula I; and/or a pharmaceutical carrier, and/or a diluent; and the formula I is expressed as follows:

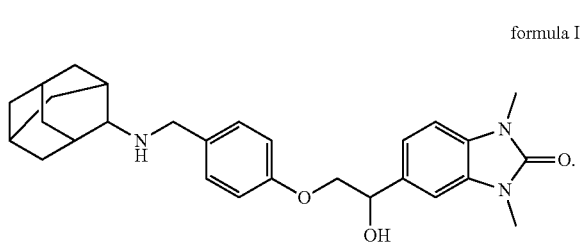 [SMILES: Cn1c(=O)n(C)c2cc(C(O)COc3ccc(CNC4C5CC6CC(C5)CC4C6)cc3)ccc21]

formula I

The disclosure has beneficial effects as follows.

(1) the compound I (also referred to as SLD-1) in the disclosure is an active small molecule targeting AIM2 protein, and the compound or the medicine prepared by the compound is used for treating psoriasis. Compared with traditional broad-spectrum immunomodulators, the compound I has a stronger targeting effect, and is more accurate, rapid, effective, safe and stable. Furthermore, the compound I has a strong binding force with human AIM2 protein and mouse AIM2 protein, and binding constants are as high as 1.029E-5M and 1.033E-5M respectively.

(2) a target point of the compound and the prepared medicine thereof for binding inhibition in psoriasis is located at upstream of an AIM2 pathway. Compared with the traditional biological inhibitors (where the biological inhibitors all act on a middle and a downstream psoriatic immune-inflammatory pathway, belong to symptomatic treatment, have unstable maintenance on the treatment effect, and greatly increase a recurrence rate of almost all the biological inhibitors after stopping medication for half a year), a blocking level to inflammatory factors is higher, and the long-term effect is more considerable than that of the biological inhibitors. Moreover, most of traditional biological agents are system injection medicines, which are very easy to affect other systems. However, the compound in the disclosure is easy to absorb for external use, which can avoid many side effects caused by system administration, and have advantages of high safety, wide applicable population, convenient administration and good compliance.

(3) The compound of the disclosure is a white crystal small molecule in a liquid form or dissolved in a colorless solvent in a colorless and clear state, and can increase applicability and aesthetics of external use on the skin after being prepared into the medicine.

Figure 1:
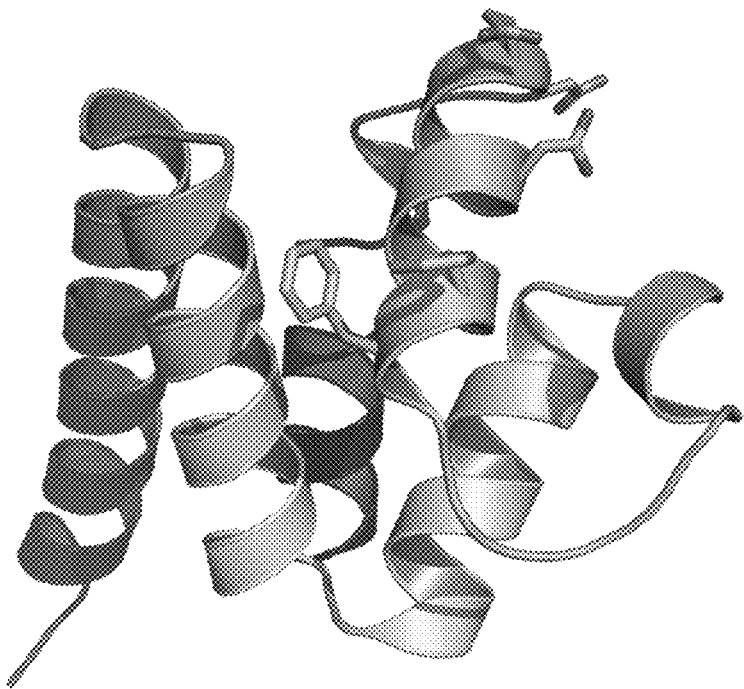
FIG. 1 illustrates a schematic crystal structure of absent in melanoma 2 (AIM2) protein.

Among them, D300-0270 refers to a compound involved in the disclosure, also referred to as the SLD-1.

DETAILED DESCRIPTION OF EMBODIMENTS

Illustrated embodiments are intended to better illustrate the disclosure and are not intended to limit the scope of the disclosure to the illustrated embodiments. Therefore, non-essential modifications and adjustments of implementation solutions by those skilled in the art according to the above disclosure still belong to the protection scope of the disclosure.

Terms used herein are used only to describe specific embodiments and are not intended to limit the disclosure. Expressions in a singular may include expressions in a plural unless they have a significantly different meaning in the context. As used herein, it should be understood that terms such as "include", "have", "contain" are intended to indicate the presence of features, numbers, operations, components, parts, elements, materials or combinations. The terms of the disclosure are disclosed in the specification and are not intended to exclude the possibility that one or more other features, numbers, operations, components, parts, elements, materials or combinations thereof may be present or may be added. As used here, "l" may be interpreted as "and" or "or" depending on the situation.

A purpose of the disclosure is to provide a use of a compound or a medicinal derivative thereof in inhibiting absent in melanoma 2 (AIM2) protein activity. The compound can be used as a medicine for treating psoriasis, which can significantly inhibit production of interleukin 1 beta (IL-1β), reduce proportions of TCRγ/CD3$^+$RORγt of imiquimod (IMQ) mice, significantly improve an inflammatory phenotype of the IMQ mice.

Specifically, the compound ($C_{28}H_{35}N_3O_3$) is shown in formula I, and the formula I is expressed as follows:

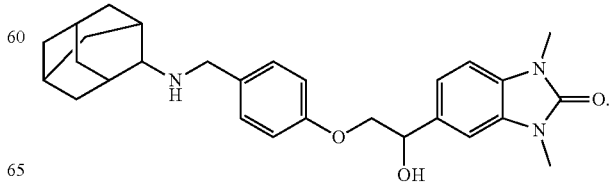

formula I

In an aspect, the disclosure provides a use of the compound or a medicinal derivative thereof in inhibiting AIM2 protein activity.

Specifically, multi-omics studies such as single-cell transcriptome sequencing, assay for transposase accessible chromatin with high-throughput sequencing (ATAC-seq), transcriptomics, genomics of psoriasis patients and imiquimod (IMQ)-induced psoriatic mice showed that only AIM2 inflammasome gene is significantly activated in both psoriatic lesions and peripheral blood. There are many susceptibility genes of psoriasis in AIM2-IL-1β-IL-17 signaling pathway, Aim2 pathway has been proved to play a crucial role in the occurrence and aggravation of psoriasis, and psoriasis-like inflammatory phenotype of IMQ mouse model can be controlled by regulating the activity of AIM2 pathway. AIM2 is an upstream initiator of the pathway, the effect of the pathway can be effectively blocked by blocking the ability of AIM2 protein to activate the downstream protein in psoriasis, which has a stronger and lasting effect than only eliminating a executive factor interleukin 17 (IL-17) in principle. Considering that blocking upstream molecules may cause other system abnormalities affected by related pathway in the traditional systematic biological treatment, the disclosure uses BiacoreT200 equipment to determine affinity between a compound and a protein model based on an amino coupling method, then screens out 100 small molecule inhibitors of AIM2 according to the affinity by a computer, and finally screens out a safer compound with an inhibitory effect in HaCaT cell model, that is, the compound shown in the formula I.

Specifically, the medicinal derivative of the compound refers to a compound obtained by retaining a mother nucleus structure and changing a structure of the compound on a basis of the mother nucleus structure. The compounds obtained by structural change can retain the effect of inhibiting the AIM2 protein activity, improve activity of the compound or improve pharmacokinetic properties.

In an embodiment, the compound is in a form of a pharmaceutical salt.

In an embodiment, the compound is in a form of a pharmaceutical acid addition salt. Of course, other forms of salt formation are not excluded.

In another aspect, the disclosure provides an application method of the compound or the medicinal derivative thereof in preparing of a medicine for inhibiting AIM2 protein activity.

In an embodiment, the medicine for inhibiting the AIM2 protein activity is a medicine of inhibiting the AIM2 protein activity of psoriatic lesion tissue. Specifically, as described above, the compound inhibits the AIM2 protein activity to treat psoriasis through the AIM2-IL-1n-IL-17 signaling pathway of psoriasis, and the compound mainly targets AIM2 to reduce the content of active caspase-1 p20 and IL-1β p17 with biological activity. It indicates that the compound only has influence on the psoriasis AIM2-IL-1β-IL-17 signaling pathway, has no influence on other systems, has a strong pertinence to psoriasis, and brings lower side effects.

In an embodiment, the compound is in a form of a pharmaceutical salt.

In an embodiment, the compound is in a form of a pharmaceutical acid addition salt.

In an embodiment, a dosage form of the medicine inhibiting AIM2 protein activity is at least one of a capsule, a tablet, an oral preparation, a microcapsule preparation, an injection, a suppository, a spray, and an ointment. Specifically, those skilled in the art can select an appropriate dosage form according to an administration route and an administration object.

In still another aspect, the disclosure provides a pharmaceutical composition for treating psoriasis, which includes at least a compound as shown in the formula I; and/or a pharmaceutical carrier, and/or a diluent. The formula I is expressed as follows:

formula I

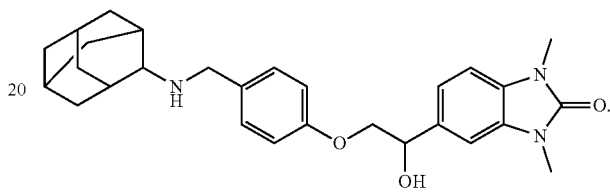

In an embodiment, the pharmaceutical carrier and/or the diluent are applicable to any one of a solution dosage form, a colloidal solution dosage form, an emulsion dosage form, a suspension dosage form, a gas dispersion dosage form, a particle dispersion dosage form, and a solid dispersion dosage form.

In an embodiment, the compound shown in the formula I may be combined with other medicines for treating psoriasis to achieve a better therapeutic effect, such as combined with a biological agent targeting downstream molecules IL-17 or IL-23, which can reduce the minimum effective dose of the biological agent, reduce an interference of the biological agent to other systems to a certain extent, and achieve a more stable and safe effect than unilateral use of the biological agent.

Specifically, a use dose of an effective component of the compound in the medicine is 2.5 milligrams per kilogram (mg/kg).

In the disclosure, the compound used for inhibiting the AIM2 protein activity is to use BiacoreT200 equipment to determine the affinity between the compound and the protein model based on the amino coupling method, then screens out 100 small molecule inhibitors of AIM2 according to the affinity by the computer, and finally screens out the compound in the disclosure with inhibitory effect in the HaCaT cell model. It specifically includes steps as follows.

(1) Selection of a Crystal Structure of AIM2 Protein

According to an amino acid sequence (as shown in SEQ ID NO: 1) and a three-dimensional structure of the AIM2 protein (Interaction-inducible protein AIM2, UniProtKB: https://www.uniprot.org/uniprot/O14862), a protein binding domain for reference is screened. There are five kinds of three-dimensional crystal structures of the AIM2 protein retrieved from RCSBPDB library, as shown in Table 1. Among them, the crystal structures 3VD8 and 4O7Q both have greater resolution, the crystal structure 3VD8 has more amino acid sequences than that of the crystal structure 4O7Q, and therefore the crystal structure 3VD8 is preferentially listed as a crystal structure for screening.

TABLE 1 three-dimensional crystal structures of AIM2 protein

| PDBentry | Method | Resolution (Å) | Chin | Position |
|---|---|---|---|---|
| 3RN2 | X-ray | 2.55 | A/B | 144-343 |
| 3RN5 | X-ray | 2.50 | A/B/C/D | 144-343 |
| 3VD8 | X-ray | 2.07 | A | 1-107 |
| 4O7Q | X-ray | 1.82 | A | 1-93 |
| 6MB2 | electron microscopy | 5.00 | A/B/C/D/E/F/G/H/I/J/K/M/N/O | 1-93 |

(2) Selection of Binding Sites

A pyrin domain (PYD) targeting AIM2 is essential for its regulation of the downstream signaling pathway. Alpha2 amino acid of the PYD is specific, and the PYD is composed of six helixes. D19, E20, D23, F27 and F28 of the alpha2 of the PYD are the most key amino acids for PYD-PYD interaction between AIM2 and a PYD of ligandin ASC. Therefore, taking the crystal structure 3VD8 as the reference, the binding sites composed of D19, E20, D23, F27 and F28 are selected for virtual screening of new small molecule inhibitors of the AIM2 protein.

Figure 2:
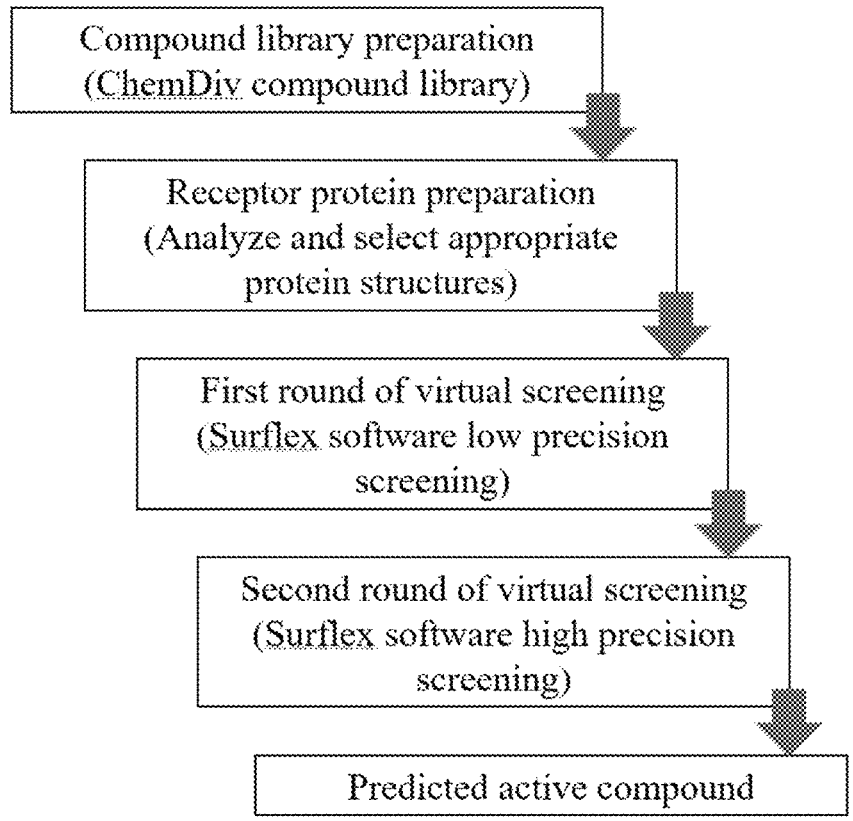
FIG. 2 illustrates a schematic flowchart of a virtual screening.
Figure 3A:
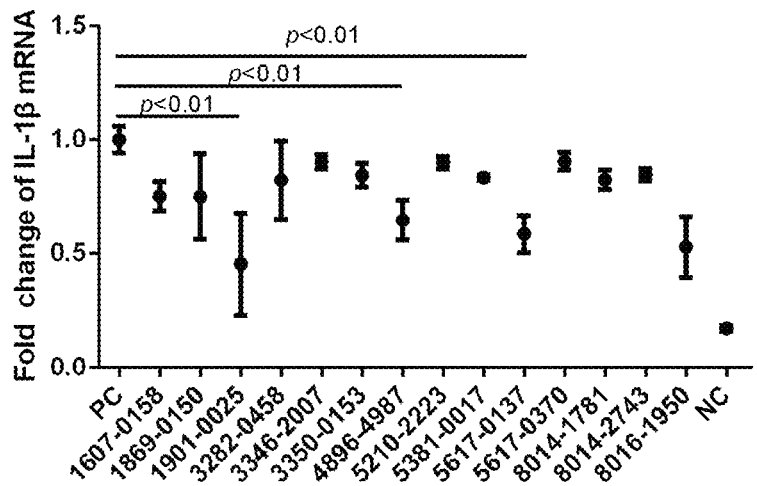
FIGS. 3A-3H illustrate detection results of interleukin 1 beta (IL-1β) in HaCaT cells messenger ribonucleic acid (mRNA) by real-time fluorescence quantitative polymerase chain reaction (PCR).
Figure 3B:
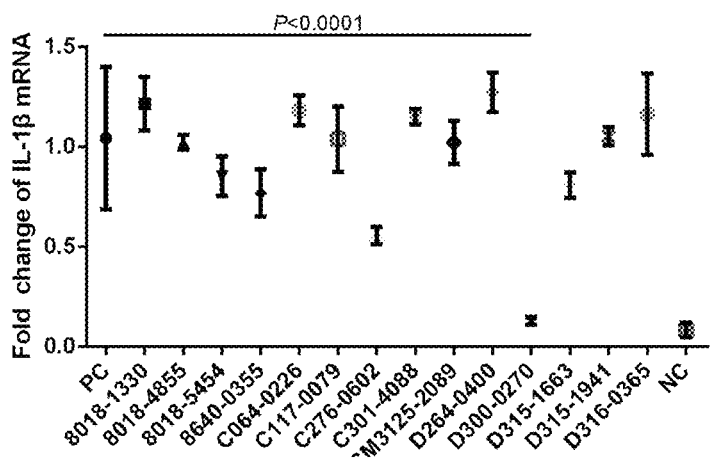
Figure 3C:
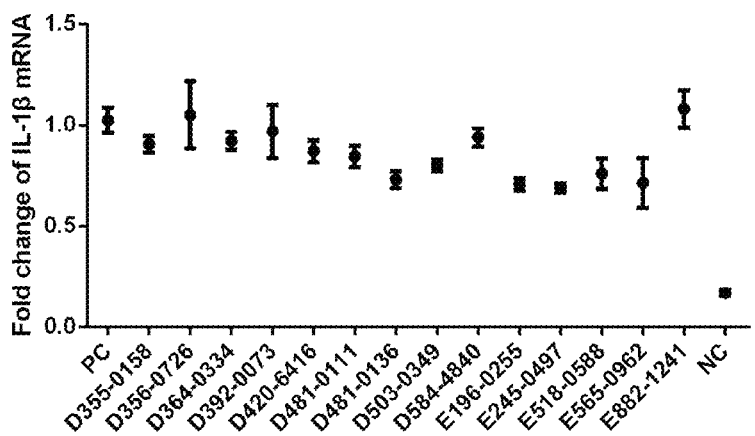
Figure 3D:
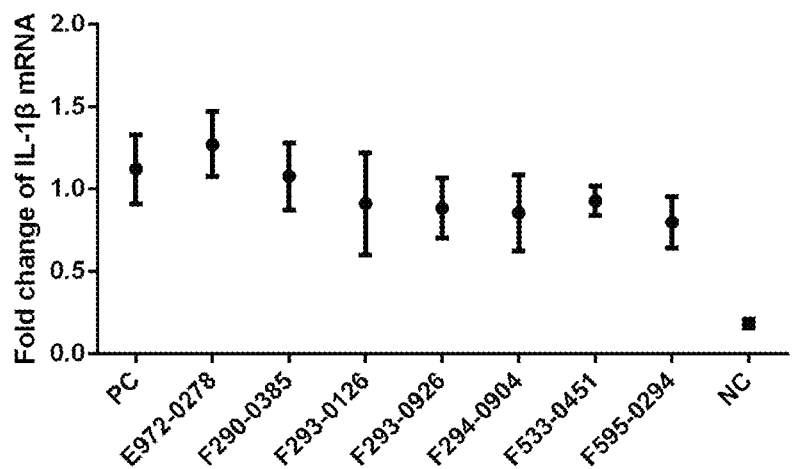
Figure 3E:
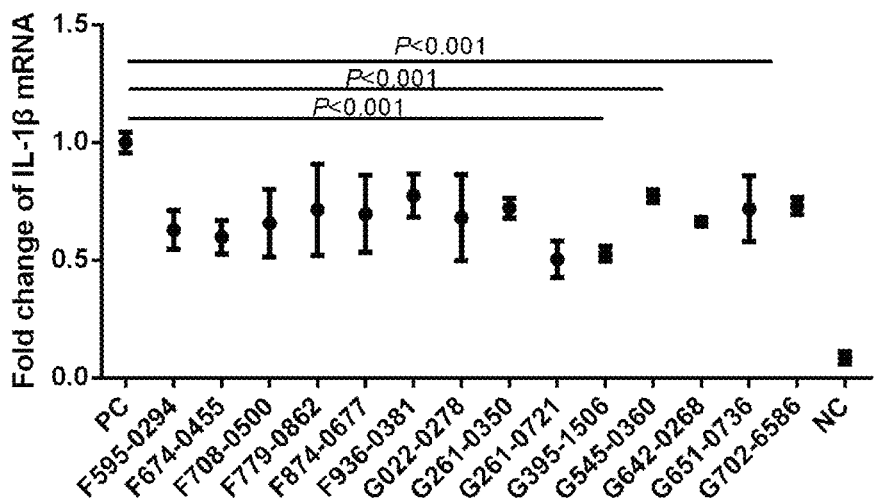
Figure 3F:
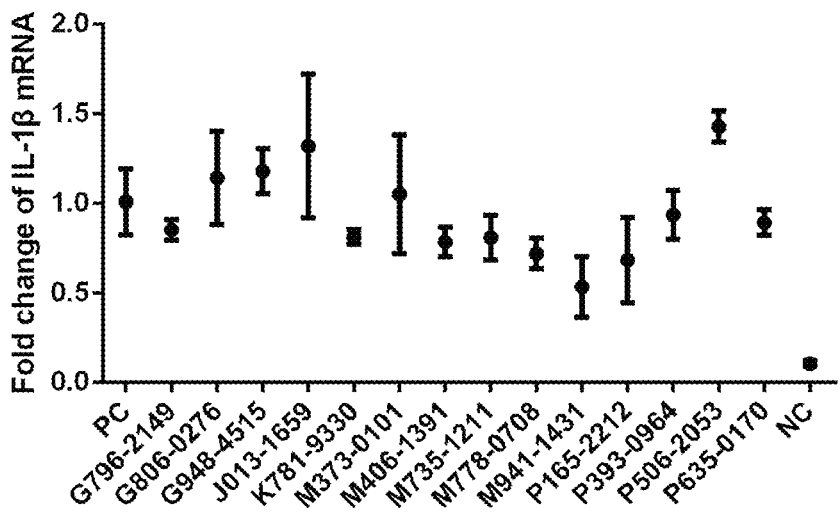
Figure 3G:
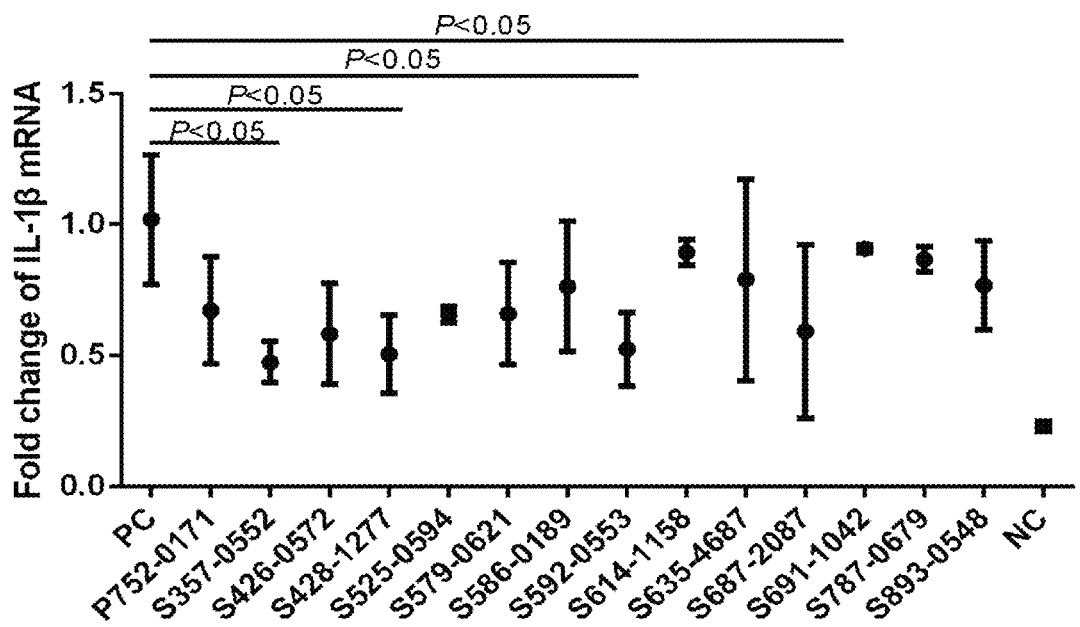
Figure 3H:
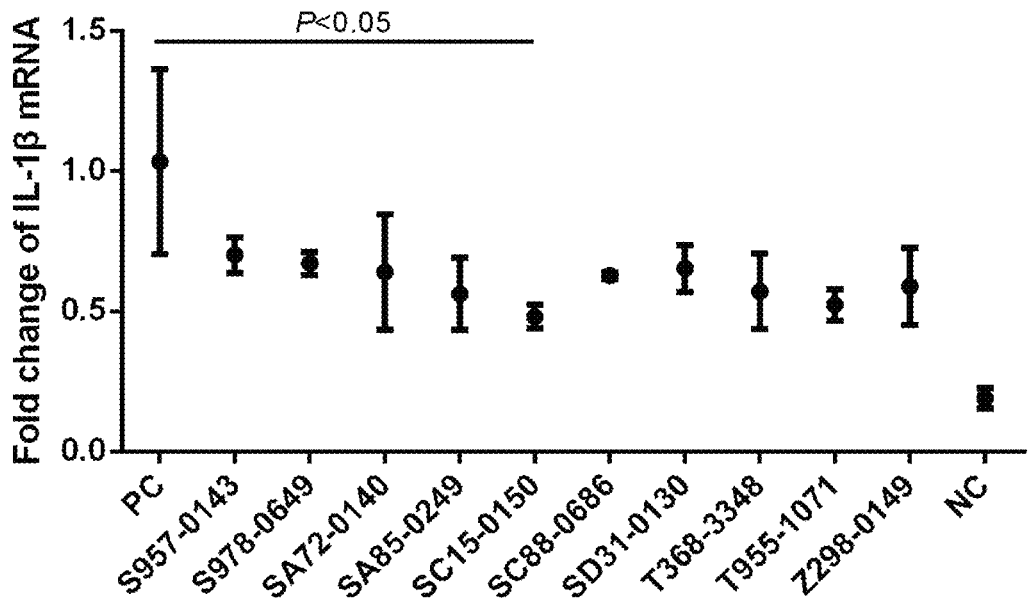

(3) Determination of a Computer VIRTUAL screening Process, a Small Molecule Compound Library, a Selection and a Preparation of a Target Protein The computer virtual screening process: the binding sites composed of D19, E20, D23, F27 and F28 of the AIM2 protein are determined to be screening sites of new small molecule inhibitors, and the three-dimensional crystal structure of AIM2 (PDBID: 3VD8) is taken as the reference (as shown in FIG. 1). Operation steps of a virtual screening plan are shown in FIG. 2.

The small molecule compound library: ChemDiv is selected for small molecule database.

The selection and the preparation of the target protein: based on the three-dimensional crystal structure of AIM2 (PDBID: 3VD8), a "Prepare Protein Structure" module of sybyl-x2.1 is used to process the AIM2 protein. All water molecules are selected in "Remove Substructures", that is, all water molecules are removed. Then, "Analyze Selected Structure" is used to analyze and modify the protein to complete an operation of hydrogenation of the protein. Finally, a protocol module of sybyl is used to select D19, E20, D23, F27 and F28 on alpha2 of the PYD to thereby generate a binding cavity file of the small molecule inhibitor in a "Residue" active site generation mode, that is, 3VD8_H-R-0.50-0.sfxc is an output file processed by the target protein.

(4) Virtual Screening Calculation

Compounds in the database are selected by using a "Compoud Filtering" module of sybyl-X2.1, and the compounds are selected according to the following rules: (a) a molecular weight is less than 700; (b) cLogP (ester-water partition coefficient) is in a range of −4 to 6; (c) a number of hydrogen bond acceptors is not more than 15; (d) a number of hydrogen bond donors is not more than 6; and (e) a number of rotatable bonds is less than 11. This project is based on the "Compound Filtering" module of sybyl medicine design platform for a preliminary screening of small molecule database. The general principle is based on the above five rules. Considering that if the preliminary screening is completely based on the five rules, the number of compounds in the small molecule database will be greatly reduced and the diversity of compounds will be significantly reduced. In this situation, the purpose of computer virtual screening is to minimize the scope of medicine screening, rather than confirm which compounds must have biological activity (experimental verification is required). Therefore, in order to increase the diversity of compounds and increase the number of lead compounds with certain biological activity, it is necessary to appropriately enlarge a parameter range of "Five Rules" in the virtual screening stage. For example, the molecular weight is appropriately set to 700, and the cLogP is used to describe the hydrophilicity/hydrophobicity of the compound, which can be widened from hydrophilic to lipophilic. Similarly, for the number of hydrogen bond donors, receptors, and rotatable bonds should be appropriately and reasonably enlarged.

1. A First Round of Virtual Screening Calculation

Screening is performed by using a Surflex module in sybyl-x2.1 software. Some molecular docking parameters are modified to speed up the first round of virtual screening and screen out small molecular compounds with a molecular scoring value of top 1%. Specifically, "Max conformations per Fragment" is changed from the default of 20 to 10, and "Max number of rotatable bonds per molecule" is changed from the default of 100 to 50. Options of default "Per-Dock Minimization" and "Post-Dock Minimization" are cancelled. The "Maximum number of poses per ligand" is changed from the default 20 to 3, that is, only the top 3 molecular conformations of each ligand molecule are retained, the docking speed is accelerated, and finally the top 1% compounds are obtained.

2. A Second Round of Virtual Screening Calculation

The second round of screening is performed by using the Surflex module in Sybyl-x2.1 software. On a basis of the top 1% hits screened in the first round, the default parameters are restored (i.e., "Max configurations per Fragment" is the default of 20, "Max number of rotatable bonds per molecule" is the default 100; default options of "Per-Dock Minimization" and "Post-dock Minimization" are selected to minimize the energy before and after compound docking, and the number of initial conformations of each molecule is increased to 4), and the target compounds of top 500 are selected for artificial screening.

3. Artificial Screening and Review

The 500 targets compounds obtained from the second round of screening are artificially screened to consider whether they could form a stable interaction with alpha2 of the PYD of AIM2 (e.g., hydrogen bond, hydrophobic, π-π stacking interaction). Specifically, compounds that can form multiple hydrogen bond interactions with Arg24, Leu72, Asn73 and other amino acids on AIM2 are screened out. In this situation, there are many hydrophobic amino acids at the binding sites, such as Phe27, Phe28, Ala36, Leu40 and Leu72, which can form a hydrophobic pocket, so that the target compounds should have more hydrogen bond donor (and receptor) groups, aromatic ring structure and hydrophobic substituents. A structure of the compound should be relatively rigid enough, that is, the number of rotating keys should not be too much. Finally, 100 compounds are selected from ChemDiv library as potential AIM2 inhibitors, as shown in Table 2.

TABLE 2

100 compounds as potential AIM2 inhibitors

| Name | Total_Score | MW | CLOGP | CLOGP_ERROR | RBC | PSA |
|---|---|---|---|---|---|---|
| E565_0962 | 7.5592 | 484.5944 | 3.8206 | 41 | 8 | 189.559 |
| D315_1941 | 7.5337 | 413.49 | 3.2575 | 41 | 5 | 169.776 |
| S635_4687 | 7.4653 | 382.5423 | 2.444 | 0 | 6 | 48.014 |
| G261_0721 | 7.3816 | 465.6076 | 4.4283 | 0 | 6 | 122.811 |
| S426_0572 | 7.2172 | 409.4815 | 1.6657 | 41 | 8 | 73.333 |
| CM3125_2089 | 7.1314 | 393.4821 | 1.8615 | 0 | 6 | 104.402 |
| G806-0276 | 7.1272 | 462.6485 | 2.4265 | 41 | 7 | 113.151 |
| S893_0548 | 7.1263 | 433.5642 | 2.341 | 41 | 9 | 74.844 |
| F294-0904 | 7.122 | 487.6116 | 1.6646 | 0 | 8 | 173.641 |
| S586_0189 | 6.9708 | 397.5138 | 1.197 | 41 | 8 | 61.747 |
| C117_0079 | 6.9675 | 476.5044 | 3.77 | 30 | 5 | 271.103 |
| S687_2087 | 6.8761 | 405.4928 | 1.0179 | 0 | 5 | 76.896 |
| S691_1042 | 6.8635 | 409.5444 | 3.169 | 41 | 7 | 56.573 |
| S614_1158 | 6.86 | 428.5246 | 1.267 | 42 | 9 | 66.933 |
| 8014_1781 | 6.8441 | 374.4754 | 4.7566 | 10 | 6 | 102.777 |
| G642_0268 | 6.8409 | 454.4342 | 4.938 | 59 | 6 | 142.86 |
| S579_0621 | 6.8267 | 418.4849 | 3.4745 | 40 | 6 | 94.401 |
| S525_0594 | 6.8049 | 422.5233 | 1.428 | 10 | 4 | 117.102 |
| G261_0350 | 6.7949 | 497.6495 | 5.5913 | 41 | 6 | 113.471 |
| G395_1626 | 6.7868 | 399.49 | −0.4106 | 30 | 9 | 111.251 |
| M735_1211 | 6.7839 | 436.5863 | 4.6829 | 0 | 9 | 45.672 |
| S357_0552 | 6.679 | 488.5781 | 0.8547 | 0 | 7 | 77.585 |
| G022_0278 | 6.6789 | 443.5822 | 4.175 | 59 | 5 | 122.935 |
| F779_0862 | 6.6704 | 371.4317 | 4.3164 | 0 | 7 | 92.409 |
| 8018_1330 | 6.6668 | 413.4238 | 4.6209 | 0 | 10 | 200.962 |
| D355_0158 | 6.6142 | 422.4736 | 4.5665 | 0 | 4 | 120.303 |
| D392_0073 | 6.6134 | 423.4848 | 2.8352 | 30 | 5 | 221.711 |
| D503_0349 | 6.6023 | 395.498 | 3.9615 | 0 | 7 | 71.266 |
| D420_6416 | 6.5841 | 402.4458 | 3.2024 | 0 | 7 | 127.837 |
| D481_0136 | 6.5774 | 450.9207 | 2.7938 | 30 | 7 | 129.027 |
| F293-0926 | 6.5708 | 499.6256 | 4.8385 | 0 | 9 | 180.677 |
| E233_1827 | 6.5554 | 467.991 | 2.8943 | 0 | 6 | 37.477 |
| F533-0451 | 6.5551 | 490.5907 | 2.6191 | 0 | 6 | 118.498 |
| G395_1506 | 6.5494 | 474.4687 | 2.1771 | 0 | 7 | 152.213 |
| D315_1663 | 6.5476 | 361.4585 | 2.8325 | 0 | 4 | 162.142 |
| E972-0278 | 6.546 | 464.6229 | 5.0156 | 59 | 8 | 76.761 |
| F293-0126 | 6.5333 | 461.5313 | 4.3922 | 0 | 9 | 213.276 |
| F674_0455 | 6.5322 | 464.9473 | 1.6044 | 0 | 5 | 59.609 |
| 8018_4855 | 6.5217 | 427.6059 | 3.5398 | 0 | 7 | 113.073 |
| P393_0964 | 6.506 | 305.3721 | 0.5028 | 0 | 4 | 65.458 |
| S957_0143 | 6.4915 | 471.5146 | 2.4851 | 30 | 6 | 110.685 |
| 1607-0158 | 6.4908 | 318.3691 | 4.2875 | 0 | 3 | 114.84 |
| M778-0708 | 6.4673 | 444.5686 | 5.0482 | 0 | 8 | 70.046 |
| F874_0677 | 6.4653 | 378.4674 | 3.929 | 41 | 5 | 55.226 |
| P752-0171 | 6.4594 | 325.4048 | 1.5889 | 0 | 5 | 70.096 |
| SC88_0686 | 6.4507 | 456.4899 | 1.648 | 41 | 5 | 137.639 |
| 8640_0355 | 6.4504 | 417.5201 | 4.1948 | 0 | 5 | 177.629 |
| T955_1071 | 6.4438 | 438.5194 | 0.516 | 0 | 8 | 112.665 |
| 5210_2223 | 6.4239 | 423.4848 | 3.0019 | 0 | 8 | 178.752 |
| C064_0226 | 6.4169 | 465.5149 | 4.3242 | 0 | 8 | 115.158 |
| D481_0111 | 6.3988 | 410.4695 | −0.1508 | 30 | 7 | 131.917 |
| S592_0553 | 6.387 | 435.4444 | 3.263 | 41 | 6 | 118.393 |
| S428_1277 | 6.3716 | 475.5031 | −1.0901 | 30 | 7 | 174.2 |
| G702_6586 | 6.3576 | 463.9592 | 5.2863 | 0 | 8 | 71.04 |
| E196_0255 | 6.3442 | 431.4853 | 3.5329 | 30 | 6 | 90.663 |
| D316_0365 | 6.3352 | 421.4657 | 4.9183 | 42 | 7 | 103.16 |
| G545_0360 | 6.3345 | 472.5787 | 4.7372 | 30 | 7 | 93.843 |
| G651_0736 | 6.3233 | 451.462 | 3.4 | 59 | 3 | 129.509 |
| S787_0679 | 6.3129 | 394.5099 | 1.3327 | 0 | 8 | 75.099 |
| D300_0270 | 6.3069 | 461.5958 | 5.143 | 0 | 7 | 83.883 |
| D356_0726 | 6.3016 | 422.5398 | 3.9 | 41 | 5 | 101.029 |
| F595-0294 | 6.2971 | 397.4691 | 4.1392 | 0 | 6 | 105.667 |
| T158_1077 | 6.2945 | 395.5196 | 0.4552 | 0 | 7 | 69.844 |
| F684_0309 | 6.2905 | 483.555 | 2.9066 | 20 | 8 | 151.851 |
| SA72_0140 | 6.2882 | 422.52 | 1.088 | 30 | 9 | 65.436 |
| 1869-0150 | 6.2643 | 519.6369 | 3.031 | 0 | 4 | 188.826 |
| P165_2212 | 6.2547 | 414.4565 | 2.0833 | 41 | 5 | 96.826 |
| 5381_0017 | 6.2481 | 331.3895 | 0.6487 | 59 | 1 | 219.333 |
| D264_0400 | 6.2469 | 429.5142 | 5.001 | 41 | 4 | 124.271 |
| 3346_2007 | 6.2448 | 386.5028 | 5.156 | 0 | 7 | 45.596 |
| M373-0101 | 6.2234 | 390.4533 | 4.2862 | 30 | 6 | 61.904 |
| 4896_4987 | 6.2132 | 488.3146 | 5.5062 | 0 | 6 | 202.076 |
| P635-0170 | 6.205 | 391.4662 | 1.9592 | 30 | 5 | 90.813 |
| S978_0649 | 6.2041 | 401.5224 | 2.069 | 41 | 6 | 80.792 |
| K781-9330 | 6.1869 | 467.5556 | 4.8946 | 0 | 5 | 112.314 |
| G948-4515 | 6.1866 | 468.5685 | 3.6211 | 0 | 6 | 136.406 |

TABLE 2-continued 100 compounds as potential AIM2 inhibitors

| Name | Total_Score | MW | CLOGP | CLOGP_ERROR | RBC | PSA |
|---|---|---|---|---|---|---|
| E518_0588 | 6.1861 | 446.5133 | 3.4234 | 0 | 10 | 83.312 |
| M406-1391 | 6.1846 | 441.5216 | 4.6336 | 10 | 5 | 133.062 |
| D584_4840 | 6.1693 | 413.4717 | 2.2059 | 30 | 4 | 74.045 |
| 5617_0137 | 6.164 | 307.3432 | 4.4807 | 0 | 4 | 101.818 |
| F936_0381 | 6.1541 | 464.5567 | 3.6814 | 59 | 7 | 107.32 |
| F708_0500 | 6.1501 | 423.5048 | 2.399 | 10 | 5 | 87.833 |
| 8018_5454 | 6.1473 | 418.4635 | 2.8449 | 0 | 5 | 153.539 |
| E245_0497 | 6.1466 | 462.5376 | 3.4682 | 0 | 7 | 155.99 |
| E882-1241 | 6.1263 | 452.5079 | 0.2355 | 0 | 7 | 215.127 |
| D364_0334 | 6.1207 | 408.4073 | 3.1987 | 59 | 5 | 165.049 |
| F290-0385 | 6.1102 | 497.5634 | 3.7437 | 0 | 8 | 201.438 |
| S343_1286 | 6.0982 | 372.4183 | 1.2493 | 0 | 5 | 111.78 |
| F270-0404 | 6.0751 | 411.4543 | 0.2083 | 0 | 7 | 125.982 |
| T842-2472 | 6.0729 | 442.5743 | 3.4651 | 0 | 6 | 72.612 |
| Z298-0149 | 6.0541 | 463.5702 | 4.3477 | 41 | 5 | 69.312 |
| SD31_0130 | 6.0451 | 438.4731 | −0.118 | 0 | 7 | 133.527 |
| C301_4088 | 6.0442 | 375.4453 | 3.3456 | 0 | 5 | 150.499 |
| 8014_2743 | 6.0381 | 394.4635 | 3.6436 | 10 | 7 | 111.958 |
| G796-2149 | 6.0351 | 383.5303 | 4.2273 | 0 | 6 | 52.129 |
| S511_0490 | 6.0317 | 381.5111 | 1.553 | 0 | 5 | 77.366 |
| M941-1431 | 6.0291 | 437.5346 | 4.301 | 30 | 7 | 63.108 |
| T368-3348 | 6.0266 | 423.4633 | 2.5063 | 0 | 4 | 101.128 |
| SA85_0249 | 6.0222 | 357.4467 | 3.1124 | 30 | 6 | 121.01 |
| P506-2053 | 6.0216 | 446.5447 | 3.8363 | 41 | 6 | 65.349 |

(5) Screening Compounds with Inhibitory Effect in the HaCaT Cell Model

The protective ability of 100 compounds screened above against cell pyroptosis of HaCaT cells stimulated by OligodA-T is evaluated by the real-time fluorescent quantitative polymerase chain reaction (PCR) detection of IL-1β mRNA in the stimulated cells. Compared with the positive control, the small molecule with the most significant inhibitory effect (p<0.0001) is selected as the candidate ideal inhibitor, that is, the compound I (also referred to as SLD-1 or D300-0270) used in the disclosure.

1. Positive control (PC) and negative control (NC) are set in the experimental group. An inclusion of Lip3000 (Lipofectamine™ 3000 Transfection Reagent) and OligodA-T (OligodA-T:Lip3000:P3000=1:1:25, a concentration of OligodA-T is 1 microgram per millimeter (ug/mL)) is used to transfect HaCat cells. Lip3000-OligodA-T and 10 micromoles per liter (uM) small molecule inhibitor are used to transfect the HaCat cells in each treatment group, and only the same amount of transfection reagent (Lip3000:P3000=1:1) is added in NC group.

2. Each experimental group is incubated in a cell incubator containing 5% $CO_2$ for 24 hours at 37° C., and the cells are collected for real-time fluorescence PCR detection. Among the 100 small molecule inhibitors, the small molecule with the most significant inhibition effect (p<0.0001) is selected as the candidate ideal inhibitor. The results are shown in FIGS. 3A-3H.

A name of the small molecule compound I (also referred to as SLD-1 or D300-0270) screened in the above method is: 5-[2-[4-[(2-adamantamide)methyl]phenoxy]-1-hydroxyethyl]-1,3-dimethylbenzimidazole-2-ketone, with a molecular weight of 461.27, and a structural formula is shown in formula I;

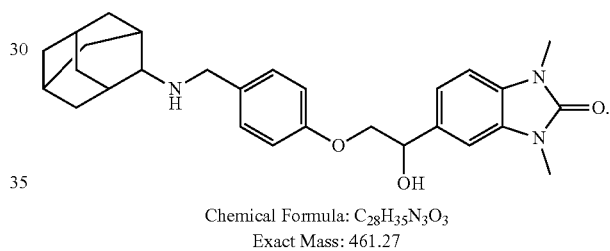

Chemical Formula: $C_{28}H_{35}N_3O_3$
Exact Mass: 461.27

The small molecule compound I screened above is characterized as follows.

Figure 4:
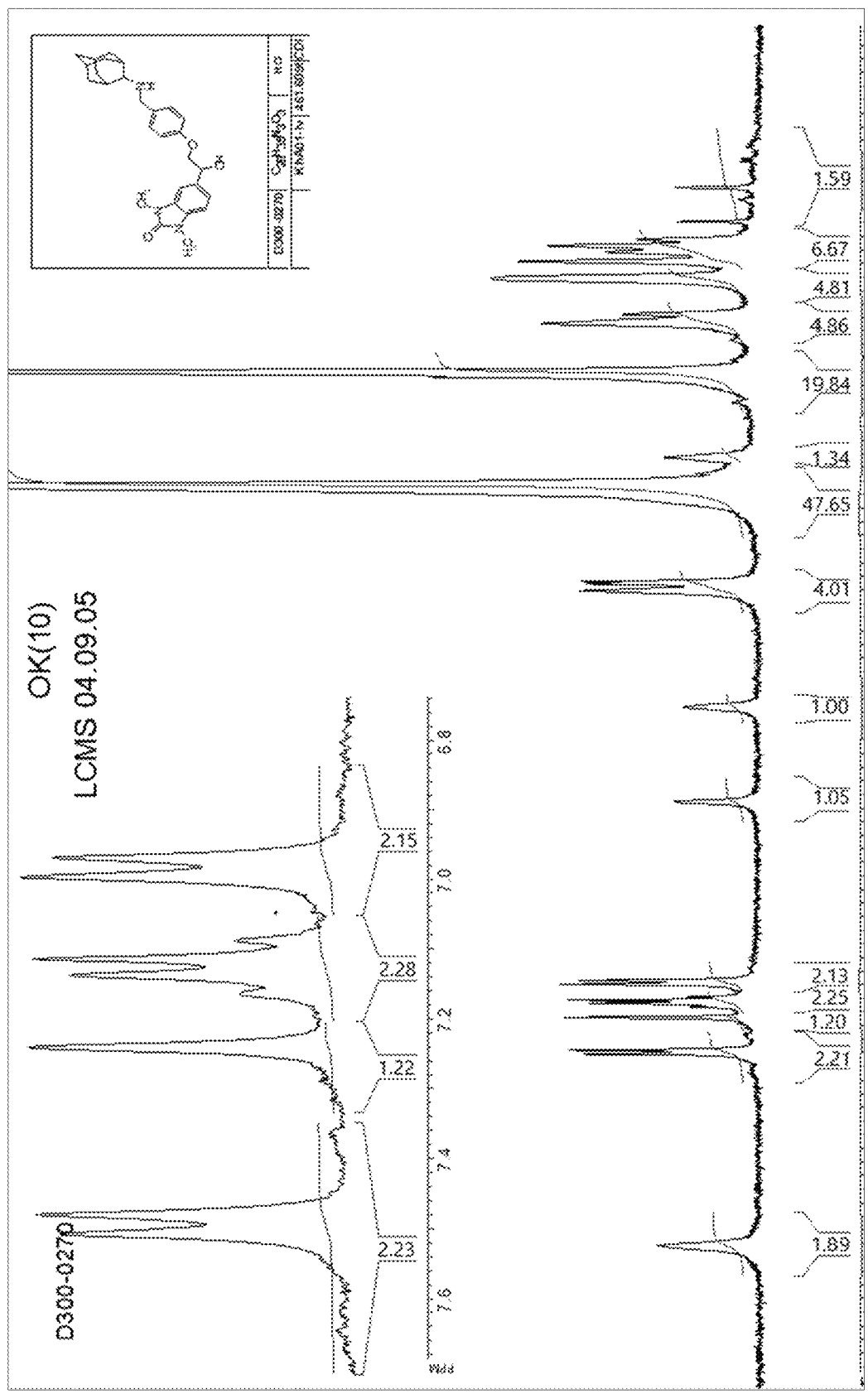
FIG. 4 illustrates a nuclear magnetic resonance (NMR) spectrum of SLD-1.

(1) A result of nuclear magnetic resonance (NMR) characterization of the small molecule compound I are shown in FIG. 4. The characteristic hydrogen and hydroxyl groups of aromatic rings are obvious, and the cleavage is clear, which is consistent with the structure of the compound, and the structure of the compound is correct.

Figure 5:
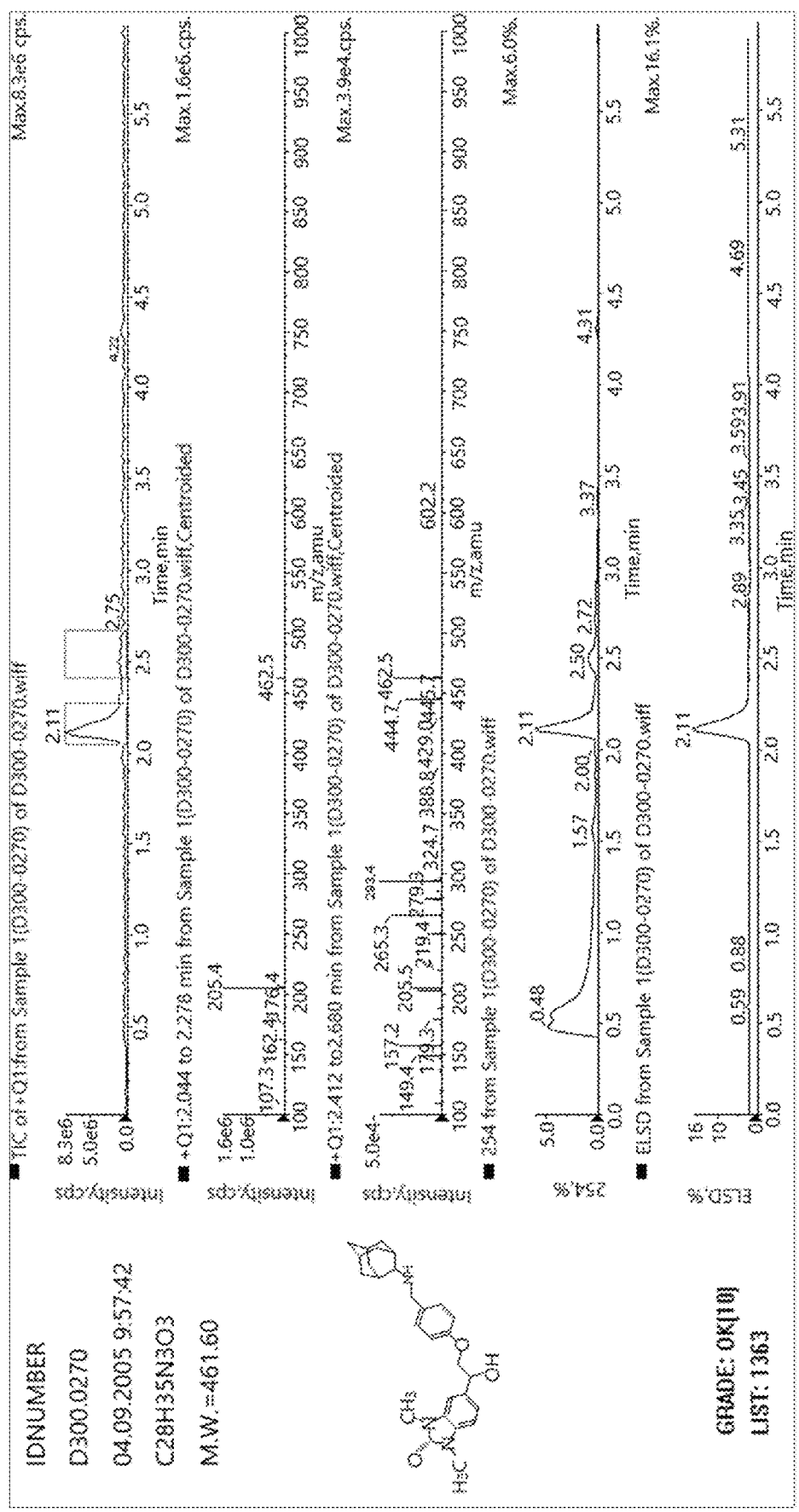
FIG. 5 illustrates a diagram of liquid chromatography-mass spectrometry (LCMS) of the SLD-1.

(2) A result of liquid chromatography-mass spectrometry (LCMS) detection of the small molecule compound I is shown in FIG. 5. The retention time is 2.11. MS+1 is a target molecular weight of the compound I, and the fragment ion peak 444.7 is the removal of hydroxyl in the compound into double bond MS+1, which is consistent with the characteristics of the target compound.

A synthetic route of the small molecule compound I screened above is as follow:

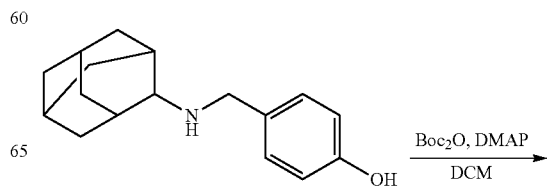

-continued

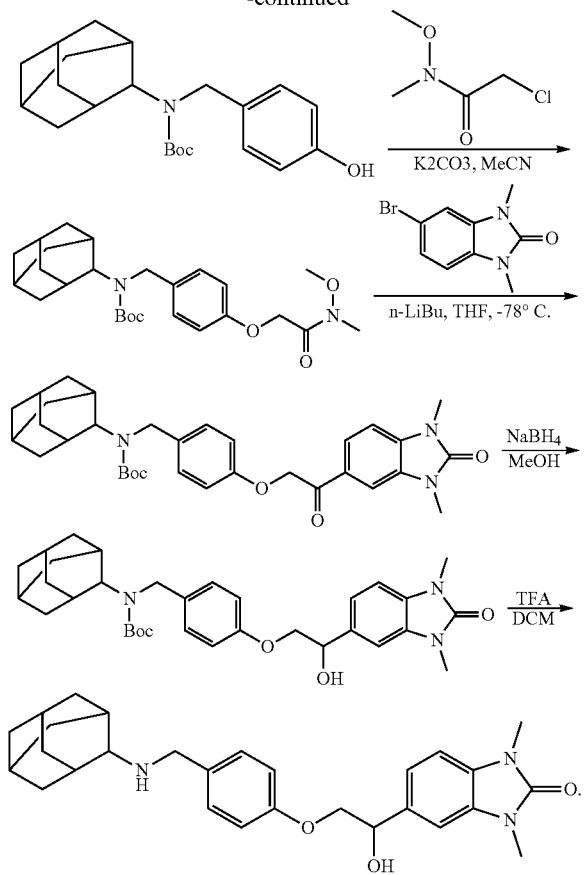

In the following embodiments, a statistical analysis of the data is performed using SPSS23.0 and RVersion 4.0.2 software for data processing and analysis. All tests are two-sided, and a P value of less than 0.05 is considered statistically significant.

In order to better understand the disclosure, the content of the disclosure is further explained in combination with specific embodiments, but the content of the disclosure is not limited to the following embodiments.

Embodiment 1 Interaction Mode Between SLD-1 and AIM2 Protein

Figure 6:
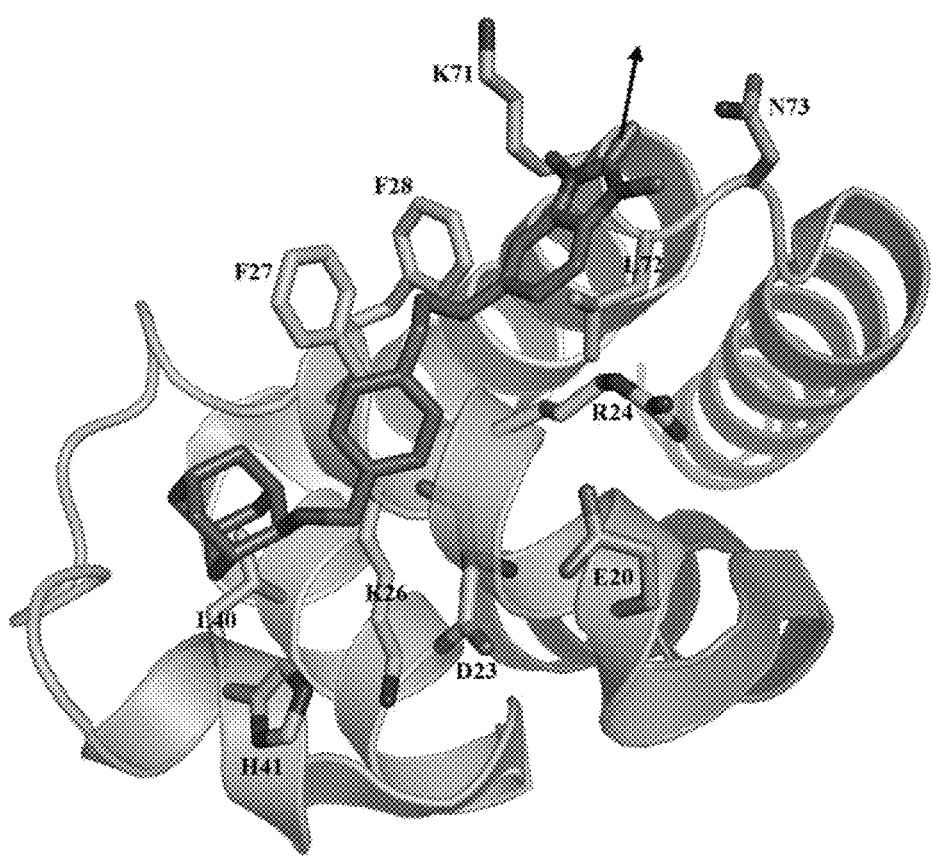
FIG. 6 illustrates a diagram showing an interaction pattern between the SLD-1 and the AIM2 protein, where an arrow indicates the SLD-1 bound to amino acid residues of the AIM2 protein, and other parts are amino acid residues of other AIM2 protein.

The structure of SLD-1 combined with AIM2 protein is simulated. Specifically, two rounds of binding simulation are performed by using a Surflex module in Sybyl-X2.1 software, and then artificial screening and reviewing are performed by forming multiple hydrogen bond interactions with Arg24, Leu72, Asn73 and other amino acids on the AIM2 protein. As shown in FIG. 6, SLD-1 has strong hydrophobic interactions with multiple hydrophobic amino acids, such as Arg24 (the hydrophobic portion of the side chain), Lys26 (the hydrophobic portion of the side chain), Phe27, Phe28, Leu40, His41, Lys71 (the hydrophobic portion of side chain) and Leu72. In addition, SLD-1 forms π-π stacking interactions with Phe27 and Phe28. It can be seen that hydrophobic π-π stacking and other interactions together maintain the binding between compound SLD-1 and the AIM2 protein.

Embodiment 2 Test of Strong Affinity Between SLD-1 and Human AIM2 Protein

Figure 7:
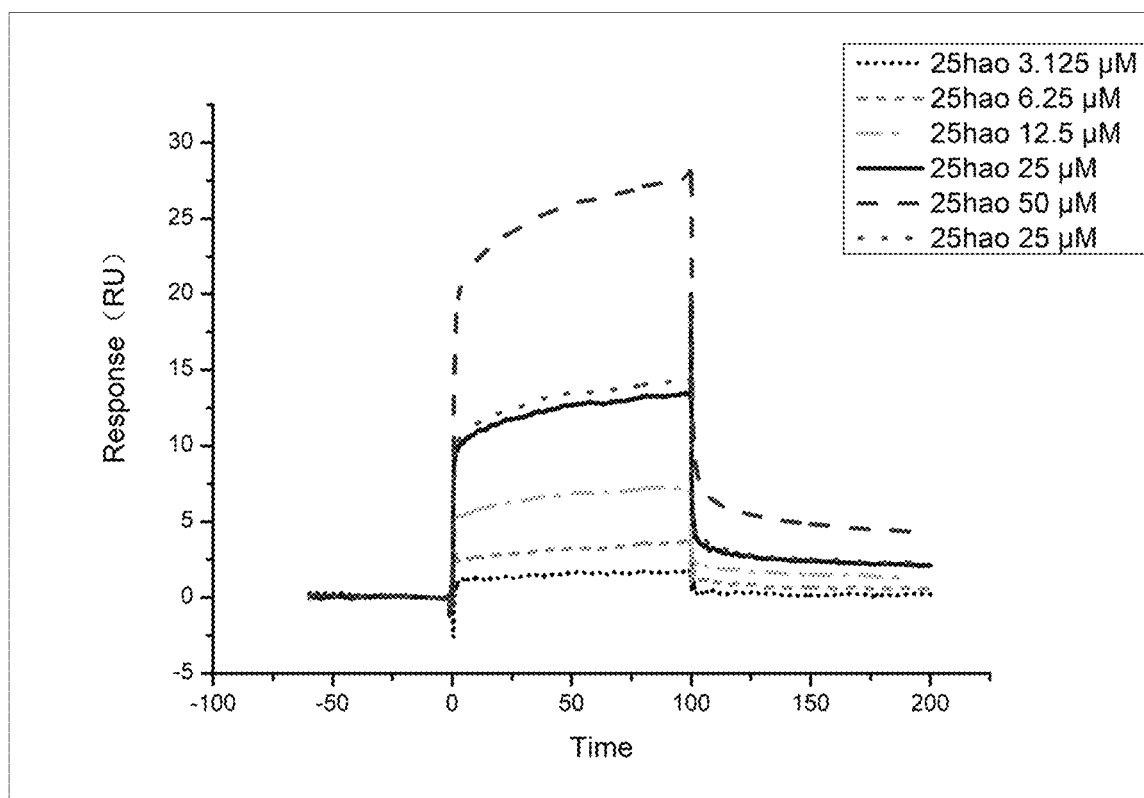
FIG. 7 illustrates a detection result of affinity between SLD-1 and human AIM2 protein.

In the embodiment of the disclosure, the affinity between SLD-1 and human AIM2 protein is detected. Specifically, a human full-length AIM2 protein is expressed and purified firstly by pET28a vector, and then the affinity is determined by CMS chip amino-coupling method through a surface-plasmon resonance (SPR) method of Biacore. A detection result is shown in FIG. 7, the result shows that SLD-1 is specifically bound to the human AIM2 protein, a binding constant is 1.029E-5M, and the binding ability is very strong.

Embodiment 3 Test of Strong Affinity Between SLD-1 and Mouse AIM2 Protein

Figure 8:
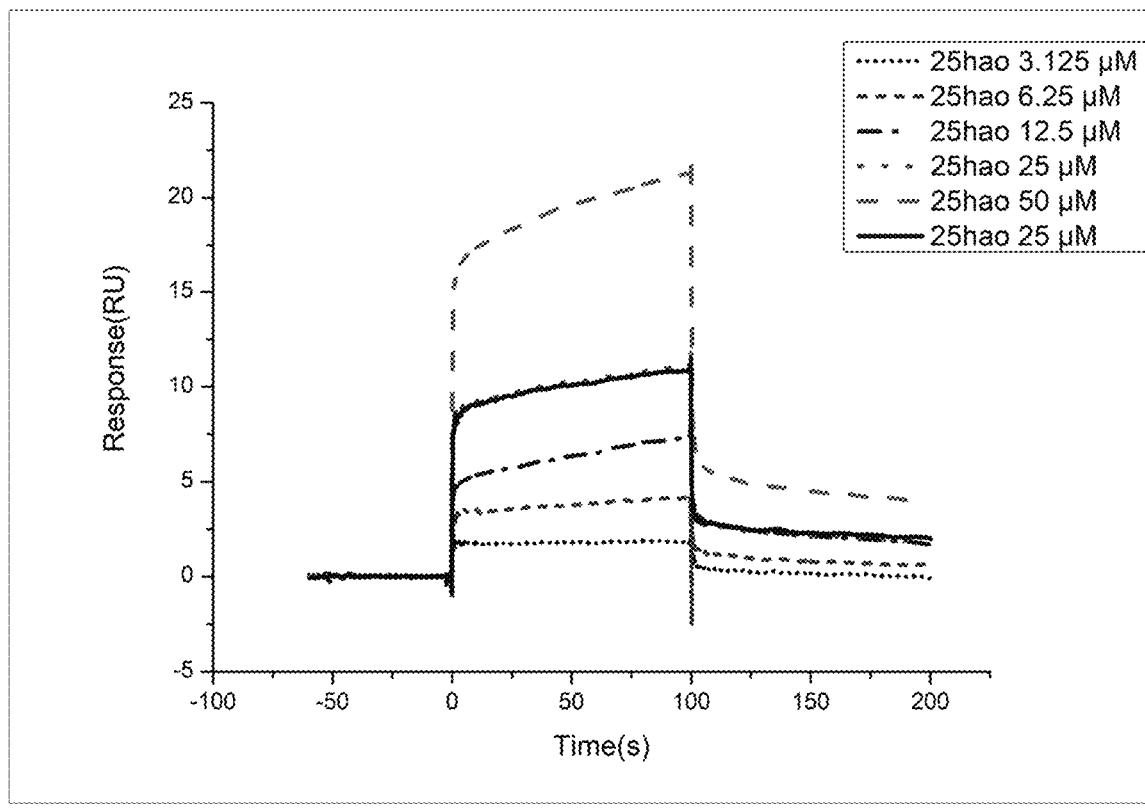
FIG. 8 illustrates a detection result of affinity between SLD-1 and mouse AIM2 protein.

In the embodiment of the disclosure, the affinity between SLD-1 and mouse AIM2 protein is detected. Specifically, a mouse full-length AIM2 protein is expressed and purified firstly by pET28a vector, and then the affinity is determined by CMS chip amino coupling method by a surface plasmon resonance (SPR) method of Biacore. A detection result is shown in FIG. 8, the result shows that SLD-1 is specifically bound to the mouse AIM2 protein, a binding constant is 1.033E-5M, and the binding ability is very strong.

Embodiment 4 SLD-1 Efficiently Inhibited AIM2 Protein Activity in a HaCaT Cell Model (1) A positive control (PC), a negative control (NC) and respective treatment groups are set. An inclusion of Lip3000 (Lipofectamine™ 3000 Transfection Reagent) and OligodA-T (OligodA-T:Lip3000:P3000=1:1:25, a concentration of OligodA-T is 1 ug/mL) is used to transfect HaCat cells, and only the same amount of transfection reagent (Lip3000:P3000=1:1) is added in NC group. The HaCat cells are co-transfected with an inclusion of Lip3000-OligodA-T at gradient doses (0.1 uM, 1 uM, 5 uM, 10 uM and 25 uM) of SLD-1 in the respective treatment groups.

Figure 9:
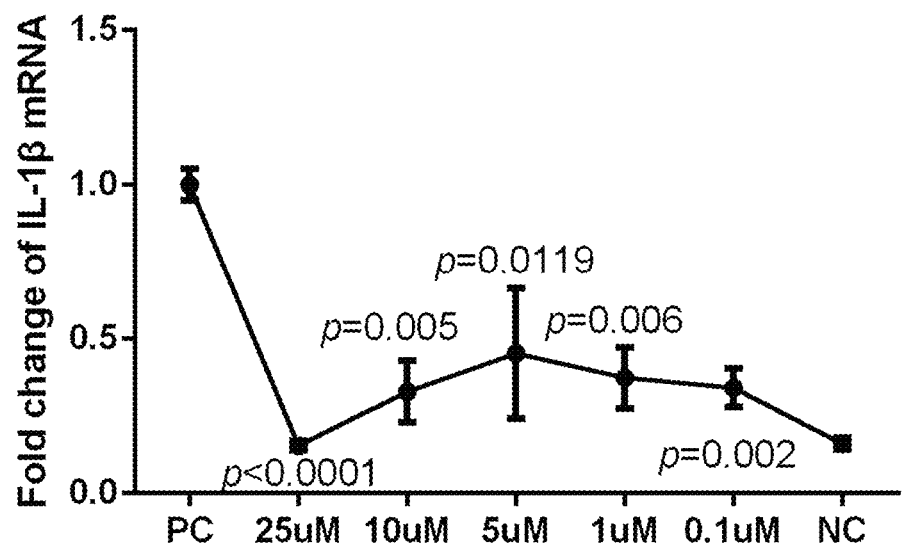
FIG. 9 illustrates transcription levels of IL-1β in the HaCaT cells treated with different doses of the SLD-1.

(2) The positive control (PC), negative control (NC) and the respective treatment groups are incubated in a cell incubator containing 5% $CO_2$ at 37° C. for 24 hours, and the cells are collected for real-time fluorescence PCR detection to observe the effect of different doses of inhibitors on the activation of AIM2 pathway in the HaCaT cells. Results are shown in FIG. 9, it can be seen that 25 uM of SLD-1 reduced IL-β transcription levels in the HaCat cells the most in 5 dose gradients compared to the PC.

Figure 10:
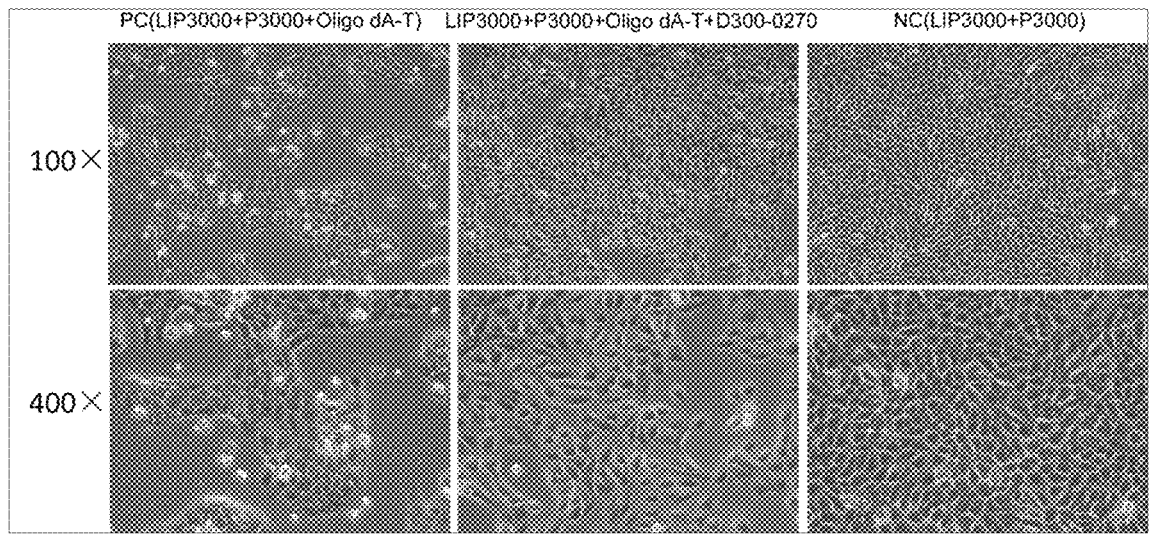
FIG. 10 illustrates morphological changes of the HaCaT cells treated with 25 micromoles per liter (uM) SLD-1.

(3) In this situation, a cell state of 25 uM gradient is observed under microscope fields of 100 times and 400 times, and results are shown in FIG. 10. The cell state of this group is close to that of the NC, with very few transparent pyroptosis cells, a high cell density and a good adhesion.

The results obtained in (2) and (3) above show that SLD-1 of 25 uM may be the best dose to inhibit AIM2 protein activity of the HaCaT cells.

Figure 11:
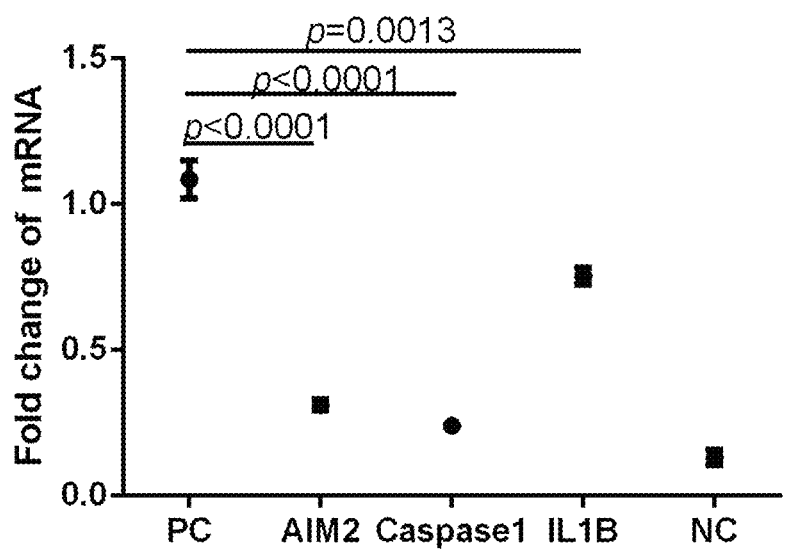
FIG. 11 illustrates AIM2 pathway gene transcription levels in the HaCaT cells treated with the 25 uM SLD-1.

(4) In addition, the effect of 25 uM of SLD-1 on the transcription level of genes in the AIM2 pathway of the HaCat cell model is detected, and results are shown in FIG. 11. Compared with the PC, the transcription of major genes in the AIM2 pathway is significantly decreased.

Figure 12:
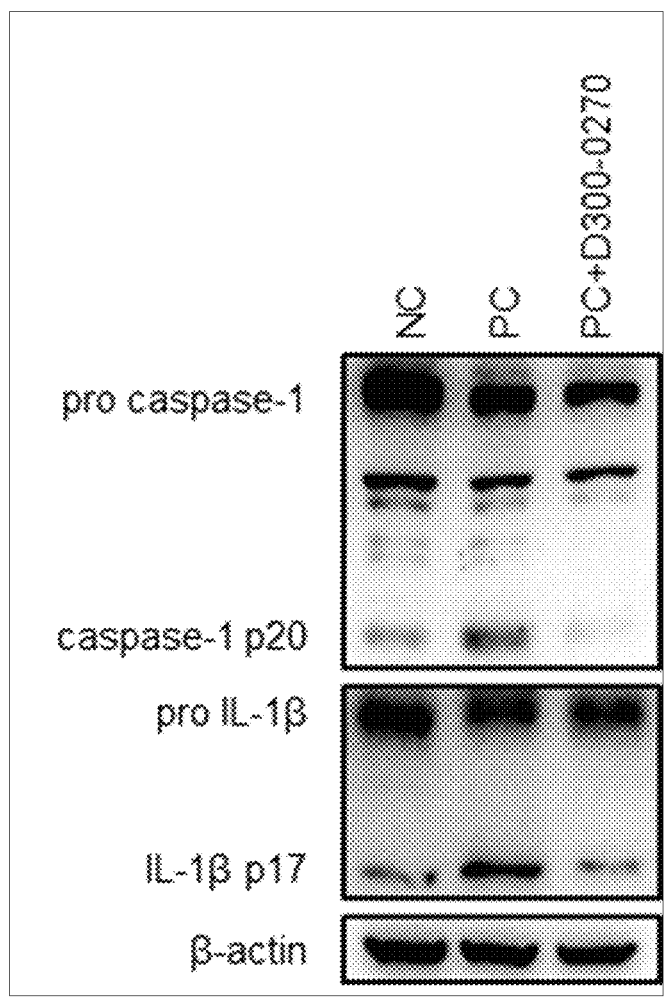
FIG. 12 illustrates AIM2 pathway protein expressions in the HaCaT cells treated with the 25 uM SLD-1.

(5) Moreover, the expression of AIM2 downstream protein in the HaCaT cells treated with 25 uM SLD-1 is detected, and results are shown in FIG. 12. The treatment of 25 uM SLD-1 has no effect on AIM2 downstream pro-caspase-1 and proIL-1β, while reduces the content of caspase-1p20 and IL-1βp17, which suggests that SLD-1 effectively reduces the expression of active caspase-1 and active IL-1β.

Embodiment 5 Test of Efficient Inhibition of AIM2 protein activity by SLD-1 in a Psoriasis Animal Model Dimethyl sulfoxide (DMSO) is used to dissolve SLD-1 powder, the powder is weighed according to different dosage, then diluted with β-cyclodextrin, and a final concentration of DMSO shall not exceed 5%. The dose gradients of SLD-1 set are 0 mg/kg, 2.5 mg/kg, 5 mg/kg and 10 mg/kg respectively. Each mouse is calculated as 20 grams (g), and 0 mg, 0.05 mg, 0.1 mg and 0.2 mg of SLD-1 are administered respective mice every day.

Seven-week-old C57/BL6 mice are selected, fed and modeled in a sun protection factor (SPF) environment. The experimental groups are as follows:
(1) mouse skin smeared with IMQ and 0 mg/kg of SLD-1;
(2) mouse skin smeared with IMQ and 2.5mg/kg of SLD-1;
(3) mouse skin smeared with IMQ and 5 mg/kg of SLD-1;
(4) mouse skin smeared with IMQ and 10 mg/kg of SLD-1;
(5) mouse skin smeared with Vaseline and 0 mg/kg of SLD-1;
(6) mouse skin smeared with Vaseline and 2.5mg/kg of SLD-1;
(7) mouse skin smeared with Vaseline and 5 mg/kg of SLD-1; and
(8) mouse skin smeared with Vaseline and 10 mg/kg of SLD-1.

Six mice in each group are shaved back hair to make a exposed skin reach 4 square centimeters. A start date of the experiment is set as day 0 and an end date is set as day 6. From day 0 to Day 5, 100 μL medicine solution is taken every day and evenly smeared mouse skin to absorb. From day 2 to day 5, each mouse 62.5 mg IMQ is smeared every day after 20 minutes of SLD-1 inhibitor. The mouse skins are scored every day, the mice are sacrificed on day 6, and skin tissue is taken for a series of tests.

Figure 13:
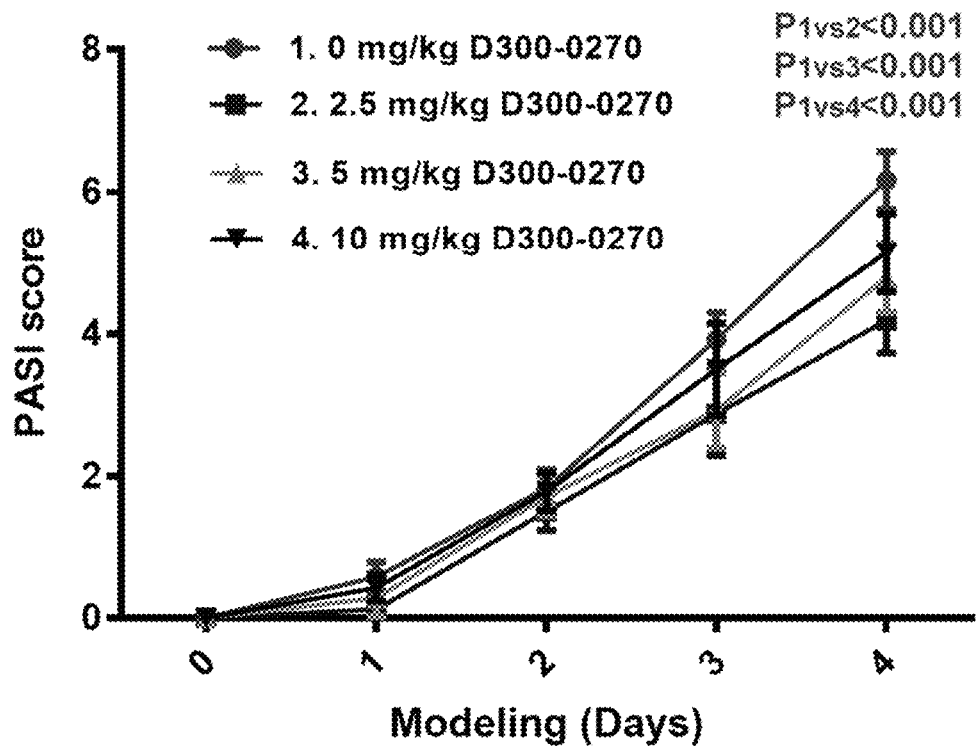
FIG. 13 illustrates psoriasis area and severity index (PASI) scores of mice in respective treatment groups.
Figure 14:
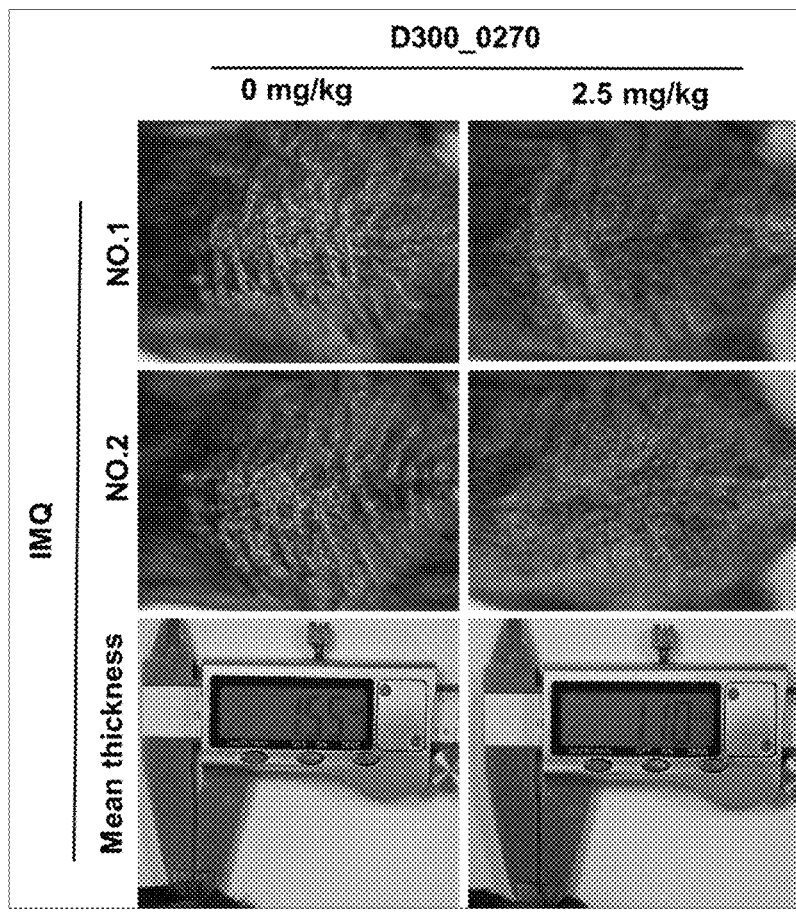
FIG. 14 illustrates a phenotype of imiquimod (IMQ) mice smeared with 2.5 milligrams per kilogram (mg/kg) SLD-1.
Figure 15:
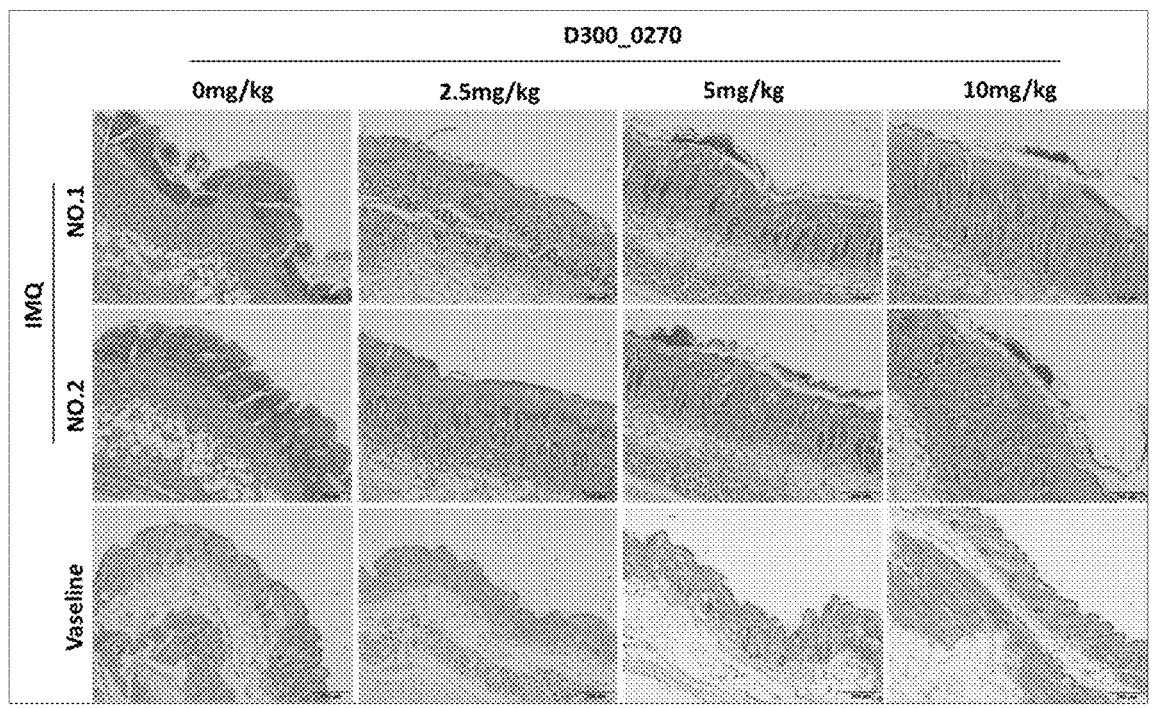
FIG. 15 illustrates skin pathological phenotypes of mice in the respective treatment groups.

PASI scores, skin phenotypes and skin pathological phenotypes of the above IMQ modeled mice are shown in FIG. 13, FIG. 14 and FIG. 15 respectively. Among them, three doses of SLD-1 reduced the inflammatory phenotype of IMQ mice to varying degrees, of which the reduction effect of 2.5 mg/kg is the most significant, and there is no difference between 5 mg/kg and 10 mg/kg.

Figure 16:
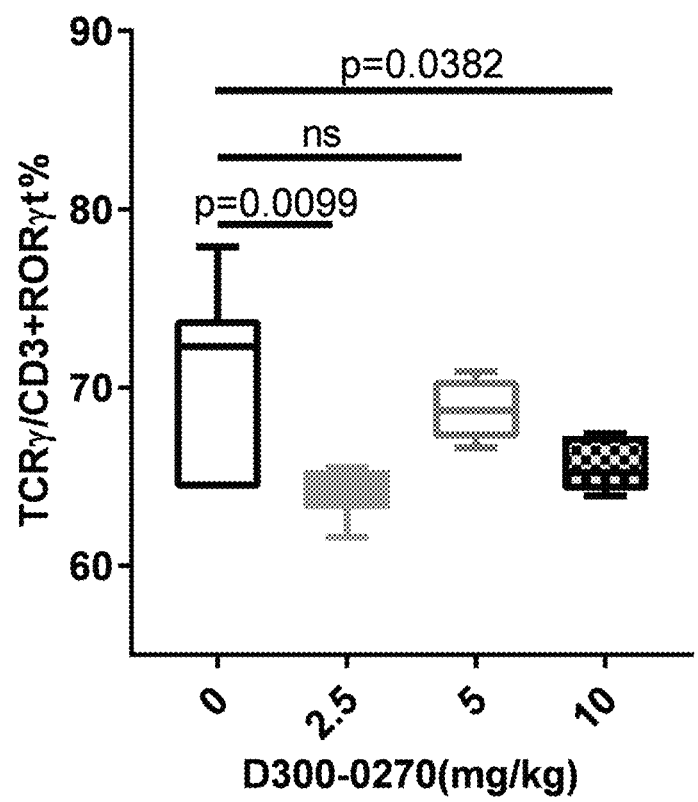
FIG. 16 illustrates a detection result of skin of mice in the respective treatment groups by flow cytometry.

Next, skin lymphocytes of the mice in each group (proportion of T lymphocytes of TCRγ/CD$^{3+}$ RORγt in the lymphocytes of mouse skin, which are the main effector cells mediated by AIM2 pathway in psoriasis and can secrete a large amount of IL-17 cytokines to aggravate psoriasis) are isolated for flow cytometry. Results are shown in FIG. 16, compared with IMQ mice without SLD-1, IMQ mice treated with 2.5 mg/kg of SLD-1 have a significantly lower proportion of TCRγ/CD3$^+$ RORγt.

Figure 17:
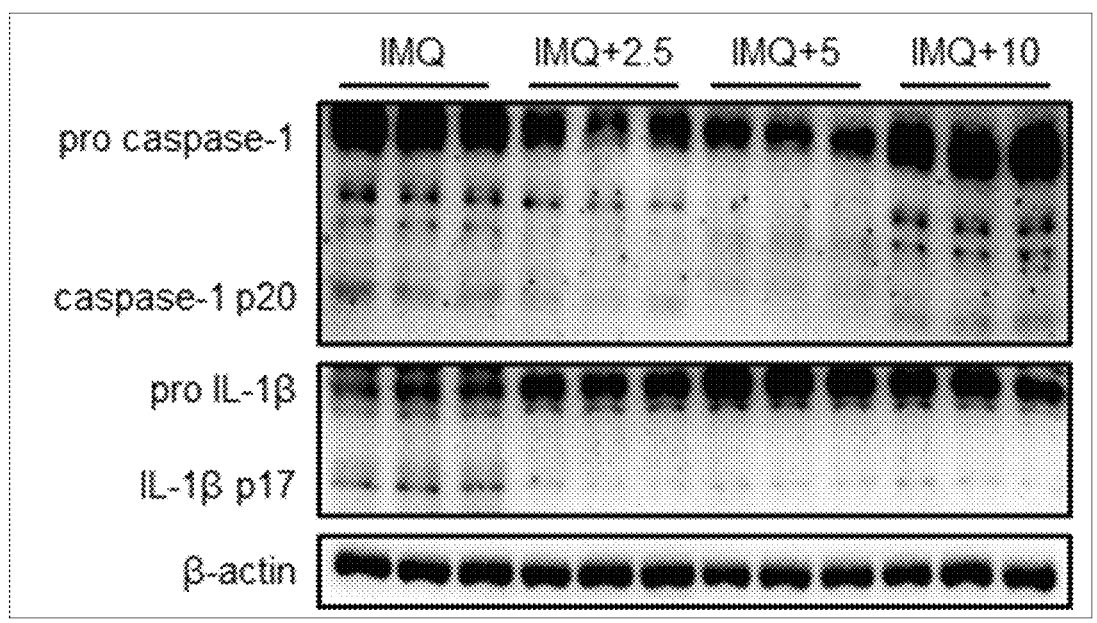
FIG. 17 illustrates AIM2 pathway protein expressions in skin of IMQ mice treated with the 2.5 mg/kg SLD-1.

Then, transcription levels of AIM2 pathway genes in the mouse skin are detected, and there is no significant difference between the respective groups. The protein levels are shown in FIG. 17. The treatment of 2.5 mg/kg of SLD-1 has no effect on AIM2 downstream procaspase-1 and proil-1β in the mouse skin, while decreases the content of caspase-1p20 and IL-1βp17, which indicates that SLD-1 effectively reduces expression of active caspase-1 and active IL-1β in skin.

Finally, the above embodiments are only used to illustrate technical solutions of the disclosure and are not limited. Although the disclosure is described in detail with reference to the preferred embodiments, those skilled in the art should understand that the technical solutions of the disclosure can be modified or equivalent replaced without departing from the purpose and scope of the technical solutions of the disclosure, which are intended to be included within the scope of the claims of the disclosure.

What is claimed is:

1. A use of a compound or a medicinal derivative thereof, comprising:

administering the compound or the medicinal derivative thereof to patients with psoriasis at a target dosage to thereby inhibit absent in melanoma 2 (AIM2) protein activity, wherein the compound ($C_{28}H_{35}N_3O_3$) is shown in a formula I, and the formula I is expressed as follows:

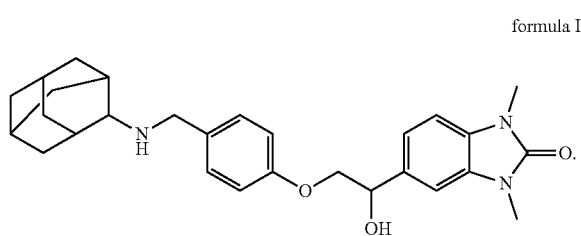 [SMILES: Cn1c(=O)n(C)c2cc(C(O)COc3ccc(CNC4C5CC6CC(C5)CC4C6)cc3)ccc21]

formula I

2. The use according to claim 1, wherein the compound is in a form of a pharmaceutical salt.

3. The use according to claim 2, wherein the compound is in a form of a pharmaceutical acid addition salt.

4. An application method of a compound or a medicinal derivative thereof, comprising:

dissolving powder of the compound or the medicinal derivative thereof with dimethyl sulfoxide (DMSO) to prepare a medicine for inhibiting AIM2 protein activity, wherein the compound is as shown in a founula I, and the formula I is expressed as follows:

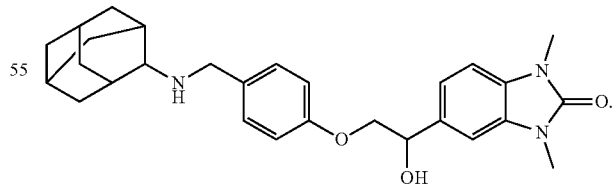

formula I

5. The application method according to claim 4, wherein the medicine for inhibiting the AIM2 protein activity is a medicine of inhibiting AIM2 protein activity of psoriatic lesion tissue.

6. The application method according to claim 4, wherein the compound is in a form of a pharmaceutical salt.

7. The application method according to claim 6, wherein the compound is in a form of a pharmaceutical acid addition salt.

8. The application method according to claim 5, wherein the compound is in a form of a phaiinaceutical salt.

9. The application method according to claim 8, wherein the compound is in a form of a pharmaceutical acid addition salt.

10. The application method according to claim 4, wherein a dosage form of the medicine for inhibiting AIM2 protein activity is at least one selected from a group consisting of a capsule, a tablet, an oral preparation, a microcapsule preparation, an injection, a suppository, a spray, and an ointment.

11. The application method according to claim 5, wherein a dosage form of the medicine for inhibiting AIM2 protein activity is at least one selected from a group consisting of a capsule, a tablet, an oral preparation, a microcapsule preparation, an injection, a suppository, a spray, and an ointment.

12. The application method according to claim 7, wherein a dosage form of the medicine for inhibiting AIM2 protein activity is at least one selected from a group consisting of a capsule, a tablet, an oral preparation, a microcapsule preparation, an injection, a suppository, a spray, and an ointment.

13. The application method according to claim 9, wherein a dosage form of the medicine for inhibiting AIM2 protein activity is at least one selected from a group consisting of a capsule, a tablet, an oral preparation, a microcapsule preparation, an injection, a suppository, a spray, and an ointment.

14. The use according to claim 1, wherein the administering the compound or the medicinal derivative thereof to patients with psoriasis at a target dosage to thereby inhibit AIM2 protein activity, comprises:
   administering the compound or the medicinal derivative thereof to the patients with psoriasis at the target dosage, and making the compound or the medicinal derivative thereof act at an upstream of an AIM2 pathway for binding inhibition in the patients with psoriasis.

15. The use according to claim 14, wherein the target dosage comprises 25 micromoles per liter (uM) of the compound or the medicinal derivative.

* * * * *